United States Patent [19]
Maas et al.

[11] Patent Number: 6,133,486
[45] Date of Patent: Oct. 17, 2000

[54] PHENOL RECOVERY FROM BPA PROCESS WASTE STREAMS

[75] Inventors: Christianus J. J. Maas, Rilland; Martin H. Oyevaar, Goes; Jos H. M. Graff, Dinteloord, all of Netherlands

[73] Assignee: General Electric Company, Schenectady, N.Y.

[21] Appl. No.: 09/222,980

[22] Filed: Dec. 30, 1998

[51] Int. Cl.$^7$ .................................................. C07C 39/12
[52] U.S. Cl. ........................................ 568/749; 568/728
[58] Field of Search ...................... 568/749, 728

[56] References Cited

U.S. PATENT DOCUMENTS

| | | | |
|---|---|---|---|
| 3,466,337 | 9/1969 | Smith | 260/621 |
| 4,277,628 | 7/1981 | Carnahan . | |
| 4,327,229 | 4/1982 | Mendiratta . | |
| 4,337,334 | 6/1982 | Shimizu | 528/137 |
| 4,346,247 | 8/1982 | Faler et al. . | |
| 4,351,966 | 9/1982 | Flock . | |
| 4,396,728 | 8/1983 | Faler . | |
| 4,400,555 | 8/1983 | Mendiratta . | |
| 4,424,283 | 1/1984 | Faler et al. . | |
| 4,584,416 | 4/1986 | Pressman et al. . | |
| 4,766,254 | 8/1988 | Faler et al. . | |
| 4,847,433 | 7/1989 | Kissinger . | |
| 5,315,042 | 5/1994 | Cipullo et al. . | |
| 5,430,199 | 7/1995 | Caruso | 568/724 |
| 5,504,251 | 4/1996 | Dyckman | 568/754 |
| 5,672,774 | 9/1997 | Dyckman | 568/749 |

FOREIGN PATENT DOCUMENTS

| | | |
|---|---|---|
| 98/52895 | 11/1998 | WIPO . |
| 98/52896 | 11/1998 | WIPO . |
| 98/52897 | 11/1998 | WIPO . |

OTHER PUBLICATIONS

Formation and Cleavage of Dihydroxydiarylmethane Derivatives, by Dr. H. Schnell and Dr. H. Krimm, Angew. Chem.internat.Edit/ vol. 2 (1963)/No. 7, pp. 373–379.

Preparation of Vinylphenols and Isopropenylphenols, by B.B. Corson, W.J. Heintzelman, L.H. Schwartzman, H.E. Tiefenthal, R.J. Lokken, J.E. Nickels, G.R. Atwood & F.J. Pavlik (Contribution from the Mellon Institute, Received Sep. 20, 1957).

*Primary Examiner*—Michael L. Shippen

[57] ABSTRACT

The disclosure is of a process for recovering valuable phenol and acetone from by-products of the condensation of phenol and a ketone from a mother liquor obtained for example upon crystallization of a 1:1 adduct of phenol and bisphenol, the mother liquor containing phenol, bisphenol, isomers, contaminant by-products of the condensation reaction of phenol with the ketone and acidic impurities. The mother liquor is distilled/evaporated leaving a tarry residue, which is the feedstock for the process of the invention. The recovery comprises catalytically cracking the feedstock with catalytic proportions of an aromatic sulfonic acid to extract the bisphenol-A values as phenol and acetone.

13 Claims, No Drawings

PHENOL RECOVERY FROM BPA PROCESS WASTE STREAMS

BACKGROUND OF THE INVENTION

1. Field of the Invention

The invention relates to processes for synthesis of bisphenols and more particularly to recovery of phenol from waste streams, the effluent of bisphenol synthesis.

2. Brief Description of Related Art

Bisphenols are commercially prepared by condensing 2 moles of phenol with a mole of ketone in the presence of an acid catalyst. The phenol is present in a molar excess of the stoichiometric requirement. During the condensation, a number of isomeric forms of the product bisphenol are formed which are contaminants of the desired bisphenol.

Among the by-product contaminant forms of phenol and bisphenol are, for example, o,p-isomers of bisphenol, chroman I and chroman II. These contaminants are carried in the product stream from the condensation reaction zone, with water, trace quantities of acidic materials derived from the catalyst, unreacted phenol and unreacted ketone. Currently, the purification of the desired product bisphenol is a costly and multi-step procedure.

There are two commercially important processes for the synthesis of bisphenols currently in use. The earlier process is called the "HCl" process, in reference to the acidic catalyst employed, hydrogen chloride [HCl]. Briefly, glass lined vessels are charged in a batch/continuous fashion, with phenol, ketone and recycled by-products from earlier synthesis. This mixture is continually kept under a positive pressure of hydrogen chloride gas which catalyzes the formation of bisphenol.

The second commercial synthesis reaction consists of passing phenol, ketone and the recycled by-products through a stationary bed of acidic ion exchange resin (IER) catalyst. This can be done in one of two ways; first, until essentially complete ketone depletion; second, and most desirable, is "partial ketone conversion". This technology is described in U.S. Pat. No. 5,315,042 which is hereby incorporated herein by reference thereto.

Representative of more detailed descriptions of the above commercial processes for condensing phenol with acetone to obtain bisphenol-A (sometimes referred to herein as BPA) are those found in the U.S. Pat. Nos. 4,346,247; 4,396,728; 4,400,555; 4,424,283; 4,584,416; 4,766,254 and 4,847,433; all of which are incorporated herein by reference thereto. The factor shared by all of these known methods and processes is the need to purify and recover the product bisphenol in steps subsequent to the condensation reaction. Another shared factor is described in the U.S. Pat. No. 4,327,229 (incorporated herein by reference thereto) which concerns the recovery of valuable products and by-products of bisphenol-A synthesis. In U.S. Pat. No. 4,327,229 recognition is given to a problem concerning the preparative reaction effluent, which contains unreacted phenol, unreacted acetone, acid residues of the catalyst, water, tars and by-product isomers of bisphenol-A in admixture with the desired bisphenol-A.

As mentioned above, all of the commercial processes to prepare bisphenol include costly multi-step purification procedures entailing distillations, crystallizations, solvent extractions, evaporations and like procedures. Where bisphenol is separated from the contaminants and purified by crystallization, a mother liquor is obtained which contains (after dewatering) lower boiling reaction by-products, bisphenol and higher boiling reaction by-products to name a few components. A part of this mother liquor is conventionally recycled to the condensation reactor for utilization in the preparative process, but a small part is purged from the process line to maintain the quality of the desired bisphenol and to avoid build-up of the undesirable by-products in the process line. The purged mother liquor may be subjected to further treatment to extract solvents, phenol, acetone, bisphenol, water and other useful components, but there ultimately results a residual tar which is generally burned as a means of disposal. However, as stated in the U.S. Pat. No. 4,327,229, "it has been calculated that substantial amounts of phenol and re-usable bisphenol-A values can be derived from the tars and liquors derived from the process of making bisphenol-A, and there still remains the need to treat the tars and residues resulting from the initial reaction of the phenol and acetone to recover all useful products in order to enhance the value of the bisphenol-A process."

The present invention is an improvement in the utilization of the tar residues of the commercial bisphenol process, using it as a feedstock to recover phenols. The process comprises cracking the tars to obtain phenols. A preferred embodiment of the present invention is an improvement in the utilization of the tar residues of the commercial acidic ion exchange resin catalyst bisphenol process wherein phenol, acetone and recycled by-product are passed through a stationary bed of the ion exchange resin which is used as a feedstock to recover phenols.

Prior to the present invention, it was known that phenols could be recovered from the above-described tar residues by thermal cracking in the presence of aluminum compounds and molecular sieve catalysts; see for example the descriptions set forth in the U.S. Pat. No. 4,277,628 (Carnahan) and U.S. Pat. No. 4,351,966 (Flock). However, these procedures can be relatively expensive for the amount of phenol recovered. We have now developed a homogeneous catalytic cracking process based on catalysis with aromatic sulfonic acids. The process of the present invention provides quantitative phenol recovery with high purity, low cost and easy handling.

SUMMARY OF THE INVENTION

The invention comprises a process for the preparation of phenols which comprises;

providing a tarry residue of higher boiling by-products of the condensation of a phenol and a ketone obtained by distillation/evaporation of a mother liquor obtained after separation of bisphenol;

cracking the tarry residue with a catalytic proportion of an aromatic sulfonic acid; and separating the resulting phenols.

DETAILED DESCRIPTION OF THE PREFERRED EMBODIMENTS OF THE INVENTION

The method of the present invention provides an economical means to recover bisphenol-A and other valuable residues from admixture with contaminant materials resulting from the bisphenol-A preparative process in effluent streams, employing improved cracking procedures to convert bisphenol-A back to phenol and acetone. A preferred embodiment of the method of the present invention provides an economical means to recover bisphenol-A and other valuable residues from admixture with contaminant materials resulting from the acidic ion exchange resin catalyst process for producing bisphenol-A in effluent streams, employing the improved cracking procedures to convert bisphenol-A back to phenol and acetone for recycling back to the reaction step comprising reacting phenol and acetone.

The commercially important processes for preparing bisphenol-A comprise condensation of 2 moles of phenol with a mole of acetone in the presence of an acid catalyst and a stoichiometric excess of the phenol reactant; see for example the U.S. Pat. Nos. 4,766,254 and 4,847,433 mentioned above.

The reaction zone effluent is conventionally continuously withdrawn and fed to a system for separation of the desired product bisphenol-A. As mentioned earlier, this effluent comprises unreacted phenol, unreacted acetone, acid residues of the catalyst, water and by-products and isomers of bisphenol-A in admixture with the desired bisphenol-A. The isomers of interest are position isomers wherein the hydroxy groups are other than in the p-configuration. The effluent may be treated first by cooling to precipitate a crystalline 1:1 adduct of bisphenol-A with phenol, and separating the solid adduct. The remaining mother liquor generally contains appreciable quantities of residual bisphenol-A and valuable isomers thereof. It is this liquor which may provide a starting material for the method of the present invention.

At least a portion of the mother liquor may be treated by heating to a temperature within the range of from about 55° C. to 95° C. to promote isomerization of related isomers to bisphenol-A or recycled through the reaction zone described above for subsequent condensations in the process line.

A portion of the mother liquor may also be treated with ion-exchange resins, filtered, distilled to remove phenol and solvents.

The feedstock employed in the process of the present invention is obtained from a portion of the mother liquor, distilled/evaporated to leave a tarry residue of higher boiling by-products of the ketone-phenol condensation, after separation (usually by crystallization and filtration) of the desired bisphenol.

In one embodiment, the mother liquor is purged from the bisphenol-A synthesis line and subjected to distillation/evaporation under progressively (sequentially) higher vacuum/temperature conditions in order to separate the stream into four fractions. A first distillation column is operated under vacuum and temperature conditions to remove an overhead fraction containing relatively pure phenol (e.g. >97% purity). The bottoms of the first column are fed to a second distillation column. This second column operates under reduced pressures and elevated temperature conditions which remove a colored "light" fraction consisting mainly of residual isomers of bisphenol-A and Chroman along with other byproducts with known and unknown chemical structure. This lights fraction can be purged from the plant and discarded, or subjected to additional recovery by this or other processes. The bottoms of the second column are fed to a third column. The overheads of this third column typically contain 60–90% pure bisphenol-A depending on the temperature and pressure conditions used. The bottoms of the third column contain "heavies" or tars which are purged from the process and used as the feedstock in the present invention.

In another embodiment, the mother liquor is distilled in a vacuum distillation column and is removed as the bottom product. This bottom product is recycled to the bisphenol reactor but a small purge stream is fed to a second vacuum distillation column (phenol recovery column). The bottom product of this second vacuum distillation column is the tarry feed to the conversion section where, employing the process of the present invention, heavies are converted to, among other compositions, phenols. The phenols thus formed are recovered through recycling to the phenol recovery column again.

In a more general sense, the mother liquor purge stream is treated in any suitable distillation unit with one of the end products being a tarry bottom stream, this stream being the feed to the conversion treatment according to the present invention wherein the tarry feedstock is cracked with an aromatic sulfonic acid catalyst.

Aromatic sulfonic acid catalysts are a well known class of compounds as are methods of their preparation. Aromatic sulfonic acids may be represented by the general formula $RC_6H_4SO_3H$ in which R may be in any position in the phenyl ring and a preferred class may be represented by the general formula:

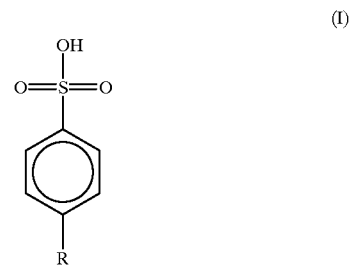

(I)

wherein R represents hydrocarbyl having 1 to 25 carbon atoms, inclusive.

The term "hydrocarbyl" as used herein means the monovalent moiety obtained upon removal of a hydrogen atom from a parent hydrocarbon. Representative of hydrocarbyl is alkyl of 1 to 25 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicysyl, docosyl, tricosyl, tetracosyl, pentacosyl and the isomeric forms thereof; aryl of 6 to 25 carbon atoms, inclusive, such as a phenyl, tolyl, xylyl, napthyl, biphenyl, tetraphenyl and the like; aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like.

The compounds of the formula (I) given above are generally well known as are methods of their preparation. Representative of the compounds (I) are p-toluenesulfonic acid and dodecylbenzene sulfonic acid.

The compound of formula (I) given above is employed as a catalyst in the catalytic cracking of the tar residues described above in a catalytic proportion. A catalytic proportion is generally within the range of from about 100 to 10,000 ppm of tar residue, preferably 1000 to 5000 ppm.

Efficient cracking occurs at temperatures of between about 100° C. to 300° C., preferably 140° C. to 250° C., and more preferably 180° C. to 200° C. at atmospheric pressure. Under these conditions quantitative amounts of phenol with high purity and low residual/nondetectable catalyst levels have been recovered. Advantageously, heating is carried out under an inert atmosphere, such as nitrogen gas atmospheres.

Progress of the reaction may be followed by conventional analytic procedures. Upon completion of the desired reaction, the product phenols may be separated by conventional techniques such as precipitation, distillation, crystallization, filtration and like procedures.

The following example and preparations describe the manner and process of making and using the invention and set forth the best mode contemplated by the inventor of carrying out the invention but are not to be construed as limiting the invention.

PREPARATION 1

A bisphenol-A process by-product stream containing approximately 83.3% phenol, 9.8% bisphenol-A, 2.3% 2-(4-hydroxyphenyl)2-(2-hydroxyphenyl) propane (o, p bisphenol-A) and 4.6% other by-products is continually passed through a jacketed "isomerization" reactor containing a bed of sulfonated polystyrene resin (Rohm & Haas Amberlyst 31) at a temperature of 74° C. At least a portion of the reaction effluent (82.5% phenol, 11.8% bisphenol-A, 1.6% 2-(4-hydroxy-phenyl)2-(2-hydroxyphenyl) propane and 4.1 % other by-products) is then passed through vessel at a temperature of 72° C. containing Rohm & Haas Amberlyst A-21 weakly basic anionic resin, an ion exchange resin, to reduce the concentration of acidic species to <2 ppm. Passing the resulting effluent solution through a filter removes particulates larger than 2 microns.

At least a portion of the resulting solution is then fed to a phenol distillation column which operates at a pressure of 30 mm of mercury and a temperature of 218° C. This removes the phenol as an approximately 99% pure colorless overhead material. The bottoms contain about 1% phenol and is continuously fed to a second distillation column which operates at a temperature of 224° C. and approximately 1–2 mm of Hg. The overhead stream from this column consists mainly of bisphenol-A isomers, primarily o, p-bisphenol-A, 2,2,4-trimethyl-4(4-hydroxyphenol), Chroman, bisphenol-A and other by-products. This stream is discarded. The bottoms is fed to a third distillation column which operates at a temperature of 260° C. to 290° C. (500–550° F.) and a pressure of 1–2 mm of Hg. The column overheads consist of circa 80+% pure bisphenol-A which can be recycled back to the bisphenol-A manufacturing process. The bottoms of the last column contain a highly colored tar (<30% bisphenol-A and >70% heavy phenolic process by-products) which is the feedstock for the following example. In a preferred embodiment of the present invention, the tar is held at a temperature of about 100° C. to 200° C. before proceeding to crack as in the following example.

EXAMPLE 1

A 250 ml three neck flask equipped with an overhead stirrer, a thermometer, a temperature controller, a condenser, a dean stark trap, a nitrogen inlet and outlet was charged with 1,000 ppm of p-toluene sulfonic acid and 60 grams of BPA Tar from Preparation 1, supra.

Using an oil bath, the charge delineated above was heated to 160° C. The reaction temperature was maintained at 160° C. for two hours along with a flow of nitrogen. Stirring of the reaction mixture was started after the reactants had melted. After two hours at 160° C., the reaction mixture was allowed to cool to 110° C., followed by the addition of 200 ml of water. At this stage, nitrogen flow was stopped.

This process provides an efficient, low cost method of recovering phenols and other materials of value from process streams which would be normally disposed of by burning. Although the process of the invention has been described above in reference to the preferred embodiment wherein the process stream or feedstock is the residual tar from a commercial production of bisphenol A, those skilled in the art will appreciate that the spirit and scope of the invention applies to the use and recovery of bisphenol values from tars resulting from processes for condensation of phenols with ketones. Thus, the process of the present invention may be used to crack bisphenols of the formula:

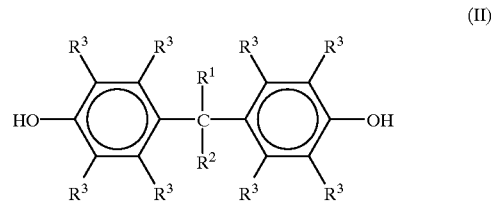

(II)

wherein $R^1$, $R^2$ and $R^3$ are alkyl. These bisphenols (II) generally result from condensation of phenols with ketones according to the schematic formula:

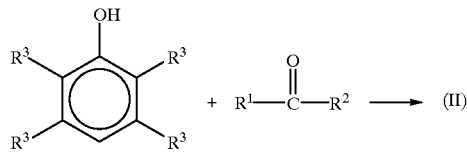

wherein $R_1$, $R_2$, and $R_3$ each independently represents hydrocarbyl as defined above.

Preferably the tars employed results from processes for the preparation of bisphenols (II) wherein $R^1$, and $R^2$ are alkyl, aryl, alkaryl, cycloalkyl, cycloalkylaryl, halogen substituted alkyl, or alkoxy; preferably having 1 to 10 carbon atoms and most preferably 1 to 6 carbon atoms. $R^3$ is preferably hydirogen, halogen, alkyl as 1 to 6 carbon atoms, cycloalkyl of 4 to 6 carbon atoms, aryl; most preferably hydrogen, alkyl of 1 to 6 carbon atoms or halogen. The process of the invention will crack these tars to recover the phenol and ketone starting reactants.

What is claimed is:

1. A process for the preparation of phenols which comprises;

providing a tarry residue of higher boiling by-products of the condensation reaction of a phenol and ketone obtained by distillation/evaporation of a mother liquor obtained after separation of bisphenol;

cracking the tarry residue with a catalytic proportion of an aromatic sulfonic acid, wherein heating is to a temperature within the range of from about 100 C. to about 300 C. under atmospheric pressures; and separating the resulting phenols.

2. The process of claim 1 wherein separation is carried out by distillation.

3. The process of claim 1 wherein the aromatic sulfonic acid is of the formula:

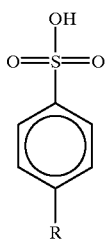

wherein R, represents hydrocarbyl of 1 to 25 carbon atoms, inclusive.

4. The process of claim 3 wherein the aromatic sulfonic acid is p-toluene sulfonic acid.

5. The process of claim 3 wherein the aromatic sulfonic acid is dodecylbenzene sulfonic acid.

6. The process of claim 1 wherein the phenol is of the formula:

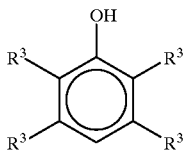

wherein each $R^3$ is independently hydrogen, halogen, hydrocarbyl or alkoxy and the ketone is of the formula:

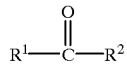

wherein $R^1$ and $R^2$ are each independently alkyl.

7. An acidic ion exchange resin process for the preparation of phenol which comprises;
  (1) providing a tarry residue of higher boiling by-products of the condensation reaction of a phenol and ketone obtained by distillation/evaporation of a mother liquor obtained after separation of bisphenol;
  (2) cracking the tarry residue with a catalytic proportion of an aromatic sulfonic acid, wherein heating is to a temperature within the range of from about 100 C. to about 300 C. under atmospheric pressures; and
  (3) separating the resulting phenols.

8. The process of claim 7 wherein the aromatic sulfonic acid is of the formula:

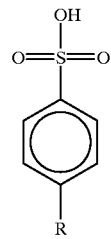

wherein R represents hydrocarbyl of 1 to 25 carbon atoms, inclusive.

9. The process of claim 8 wherein the aromatic sulfonic acid is p-toluene sulfonic acid.

10. The process of claim 8 wherein the aromatic sulfonic acid is dodecylbenzene sulfonic acid.

11. The process of claim 1 wherein the phenol is of the formula:

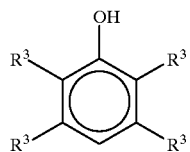

wherein each $R^3$ is independently selected from the group consisting of hydrogen, halogen, hydrocarbyl and alkoxy and the ketone is of the formula:

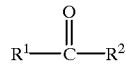

wherein $R^1$ and $R^2$ are each independently alkyl.

12. The process of claim 1 wherein the ketone is acetone.

13. The process of claim 1 wherein the reaction product of phenol and acetone is bisphenol-A.

* * * * *